(12) United States Patent
Gertzman et al.

(10) Patent No.: US 6,437,018 B1
(45) Date of Patent: *Aug. 20, 2002

(54) MALLEABLE PASTE WITH HIGH MOLECULAR WEIGHT BUFFERED CARRIER FOR FILLING BONE DEFECTS

(75) Inventors: Arthur A. Gertzman, Stony Point, NY (US); Moon Hae Sunwoo, Old Tappan, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/515,656

(22) Filed: Feb. 29, 2000

Related U.S. Application Data

(63) Continuation-in-part of application No. 09/031,750, filed on Feb. 27, 1998, now Pat. No. 6,030,635, which is a continuation-in-part of application No. 09/365,880, filed on Aug. 3, 1999, now abandoned.

(51) Int. Cl.$^7$ .............................. A61K 6/08; A61K 9/14; A61F 2/36
(52) U.S. Cl. .................... 523/116; 424/489; 623/23.61; 623/23.62; 623/23.63
(58) Field of Search ....................... 523/116; 623/23.61; 623/23.62, 23.63; 424/489

(56) References Cited

U.S. PATENT DOCUMENTS

| | | | |
|---|---|---|---|
| 2,621,145 A | 12/1952 | Sano | |
| 2,968,593 A | 1/1961 | Rapkin | |
| 4,172,128 A | 10/1979 | Thiele et al. | |
| 4,191,747 A | 3/1980 | Scheicher | |
| 4,595,713 A | 6/1986 | St. John | |
| 4,610,692 A | 9/1986 | Eitenmuller et al. | |
| 4,619,995 A | 10/1986 | Hayes | |
| 4,637,931 A | 1/1987 | Schmitz | |
| 4,963,151 A * | 10/1990 | Ducheyne | 623/16 |
| 5,073,373 A | 12/1991 | O'Leary et al. | |
| 5,106,614 A * | 4/1992 | Dowty et al. | 514/210 |
| 5,290,558 A | 3/1994 | O'Leary et al. | |
| 5,314,476 A * | 5/1994 | Prewett et al. | |
| 5,356,629 A * | 10/1994 | Sander et al. | |
| 5,507,813 A | 4/1996 | Dowd et al. | |
| 5,516,532 A | 5/1996 | Atala et al. | |
| 5,707,962 A | 1/1998 | Chen et al. | |
| 5,830,493 A | 11/1998 | Yokota et al. | |
| 6,030,635 A * | 2/2000 | Gertzman et al. | |

FOREIGN PATENT DOCUMENTS

| | | |
|---|---|---|
| EP | 0 522569 A1 | 1/1993 |
| EP | 0 784985 A1 | 7/1997 |
| WO | WO 98/14222 | 4/1998 |
| WO | WO 99/11298 | 3/1999 |
| WO | WO 99/52572 | 10/1999 |

OTHER PUBLICATIONS

Biomaterials to Reconstructive Surgery p. 314 Rubin 1978.*
Klokkevold et al., Osteogensis Enhanced by Chitosan (Poly–N–Acetyl Glucosaminoglycan) In Vitro Periodontol 1996:67:1170–1175.
Sasaki et al., Stimulation of Osteoinduction in Bone Wound Healing by High–Molecular Hyaluronic Acid Bond, vol. 16, No. 1, Jan. 1995.
Pillioni et al., Low Molecular Weight Hyaluronic Acid Increases Osteogensis in Vitro 1992 J Dent Res 71 (IADR Abstracts).
D. Cram and G. Hammond, The Carbohydrates II, pp. 43–55.
M. Iwata and M. Urist, Protein Polysaccharide of Bone Morphogenetic Matrix, "Clinical Orthopaedics and Related Research No. 87", pp. 257–273 (Sep. 1972).

* cited by examiner

Primary Examiner—Thurman K. Page
Assistant Examiner—Amy E Pulliam
(74) Attorney, Agent, or Firm—John S. Hale; Gipple & Hale

(57) ABSTRACT

The invention is directed toward a malleable bone putty and a flowable gel composition for application to a bone defect site to promote new bone growth at the site which comprises a new bone growth inducing compound of demineralized lyophilized allograft bone powder. The bone powder has a particle size ranging from about 100 to about 850 microns and is mixed in a high molecular weight hydrogel carrier contain a sodium phosphate saline buffer, the hydrogel component of the carrier ranging from about 0.75 to 4.5% of the composition and having a molecular weight of about at least 160,000 Daltons. The composition has a pH between 6.8–7.4 contains about 25% to about 35% bone powder and can be additionally provided with BMP's.

31 Claims, No Drawings

MALLEABLE PASTE WITH HIGH MOLECULAR WEIGHT BUFFERED CARRIER FOR FILLING BONE DEFECTS

RELATED APPLICATIONS

This is a continuation-in-part of U.S. patent application Ser. No. 09/031,750, filed Feb. 27, 1998 and issued into U.S. Letters Patent No. 6,030,635 on Feb. 29, 2000 and which is a continuation-in-part of U.S. patent application Ser. No. 09/365,880, filed Aug. 3, 1999, now abandoned, which is a continuation application of U.S. patent application Ser. No. 09/031,750.

FIELD OF INVENTION

The present invention is generally directed toward a surgical bone product and more specifically is a flowable gel and a malleable putty using demineralized allograft bone particles mixed in a fluid carrier having an isotonic phosphate buffer and a high molecular weight viscous excipient derived from the class of biomaterials known as hydrogels.

BACKGROUND OF THE INVENTION

Surgical implants should be designed to be biocompatible in order to successfully perform their intended function. Biocompatibility may be defined as the characteristic of an implant acting in such a way as to allow its therapeutic function to be manifested without secondary adverse affects such as toxicity, foreign body reaction or cellular disruption.

Malleable putty is used to correct surgical defects that may be caused by trauma, pathological disease, surgical intervention or other situations where defects need to be managed in osseous surgery. It is important to have the defect filler in the form of a stable, viscous putty to facilitate the placement of the bone growth medium into the surgical site which is usually uneven in shape and depth. The surgeon will take the putty on a spatula or other instrument and trowel it into the site or take it in his/her fingers to shape the bone inducing material into the proper configuration to fit the site being corrected. It is also important that the defect filler be biocompatible and have the correct osmolality and pH and not cause any additional trauma at the surgical site.

Many products have been developed in an attempt to treat this surgical need for a biocompatible bone putty or gel. One such example is autologous bone particles or segments recovered from the patient. When removed from the patient, the segments or bone particles are wet and viscous from the associated blood. This works very well to heal the defect but requires significant secondary surgery resulting in lengthening the surgery, extending the time the patient is under anesthesia and increasing the cost. In addition, a significant increase in patient morbidity is attendant in this technique as the surgeon must take bone from a non-involved site in the patient to recover sufficient healthy bone, marrow and blood to perform the defect filling surgery. This leads to significant post-operative pain.

Another product group involves the use of inorganic materials to provide a matrix for new bone to grow at the surgical site. These inorganic materials include hydroxyapatite obtained from sea coral or derived synthetically. Either form may be mixed with the patient's blood and/or bone marrow to form a gel or a putty. Calcium sulfate or plaster of Paris may be mixed with water to similarly form a putty. These inorganic materials are osteoconductive but are bioinert and do not absorb or become remodeled into natural bone. They consequently remain in place indefinitely as a brittle, foreign body in the patient's tissue.

Allograft bone is a logical substitute for autologous bone. It is readily available and precludes the surgical complications and patient morbidity associated with autologous bone as noted above. Allograft bone is essentially a collagen fiber reinforced hydroxyapatite matrix containing active bone morphogenic proteins (BMP) and can be provided in a sterile form. The demineralized form of allograft bone is naturally both osteoinductive and osteoconductive. The demineralized allograft bone tissue is fully incorporated in the patient's tissue by a well established biological mechanism. It has been used for many years in bone surgery to fill the osseous defects previously discussed.

It is well known in the art that for several decades surgeons have used a patient's own blood as a vehicle in which to mix the patient's bone chips or bone powder, or demineralized bone powder so as to form a defect filling paste. Blood is a useful carrier because it is available from the bleeding operative site, is non-immunogenic to the patient and contains bone morphogenic proteins which facilitate wound healing through new bone growth. However, stored blood from other patients has the deficiencies that any blood transfusion would have; such as blood type compatibility, possibility of transmission of disease and unknown concentration of BMP which are to a great extent dependent upon the age of the donor.

While blood contains from forty percent (40%) to fifty percent (50%) cell mass, it is a satisfactory carrier for demineralized bone powder because it contains both mono- and polysaccharides which contribute to the blood viscosity and provide the bulk viscosity to the paste created by mixing the bone powder and blood. Specific monosaccharides in blood are glucose at a concentration of 60–100 mg/100ml (0.1%) and polysaccharides such as hexose and glucosamine at approximately 0.1%. Glucuronic acid is also present at approximately 0.4–1.4 mg/100 ml (average 0.01%).

The problems inherent with using the patients blood as a carrier for demineralized bone powder are the difficulties of mixing the same at the operating site, the difficulty in obtaining a bone paste consistency which can be easily applied to the surgical area, the guesswork in mixing a usable composition at the site and the problem of having a bone paste or gel which will promote optimum bone replacement growth and not be carried away by the body fluids at the operation site or simply fall out of the bone defect site. In an attempt to solve these and other problems, there have been a number of other attempts using other alternative mixtures and compositions.

Demineralized allograft bone is usually available in a lyophilized or freeze dried and sterile form to provide for extended shelf life. The bone in this form is usually very coarse and dry and is difficult to manipulate by the surgeon. One solution to use such freeze dried bone has been provided in the form of a gel, GRAFTON®, a registered trademark of Osteotech Inc., which is a simple mixture of glycerol and lyophilized, demineralized bone powder of a particle size in the range of 0.1 cm to 1.2 cm (1000 microns to 12,000 microns) as is disclosed in U.S. Pat. No. 5,073,373.

GRAFTON works well to allow the surgeon to place the allograft bone material at the site. However, the carrier, glycerol has a very low molecular weight (92 Daltons) and is very soluble in water, the primary component of the blood which flows at the surgical site. Glycerol also experiences a marked reduction in viscosity when its temperature rises from room temperature (typically 22° C. in an operating room) to the temperature of the patient's tissue, typically 37°

C. This combination of high water solubility and reduced viscosity causes the allograft bone material with a glycerol carrier to be "runny" and to flow away from the site almost immediately after placement; this prevents the proper retention of the bone material within the site as carefully placed by the surgeon.

These problems with GRAFTON gel have been attempted to be resolved by using a much larger particle size of allograft bone, specifically lamellae or slivers of bone created by milling or slicing the bone before mixing it with the glycerol carrier. This improves both the bulk viscosity and the handling characteristics of the mixture but still leaves the problem of the fast rate of dissipation of the carrier and some bone due to the solubility of the glycerol carrier. The larger particles of demineralized bone may also retard the development of new bone by the patient because the large bony lamellae do not pack as well as the smaller grainy particles of bone. This will leave more open space and could lengthen the time required to grow new bone and properly fill the defect. Another deficiency of using the bony lamellae is that the ends of the bony fragments are uneven and when packed into the surgical defect, uneven filaments of bone are left protruding out from the defect which can compromise the healing rate.

U.S. Pat. No. 5,290,558 discloses a flowable demineralized bone powder composition using an osteogenic bone powder with large particle size ranging from about 0.1 to about 1.2 cm. mixed with a low molecular weight polyhydroxy compound possessing from 2 to about 18 carbons including a number of classes of different compounds such as monosaccharides, disaccharides, water dispersible oligosaccharides and polysaccharides.

Hence, the advantages of using the smaller bone particle sizes as disclosed in the U.S. Pat. No. 5,073,373 gel patent were compromised by using bone lamellae in the shape of threads or filaments and retaining the low molecular weight glycerol carrier. This later prior art is disclosed in U.S. Pat. Nos. 5,314,476 and 5,507,813 and the tissue forms described in these patents are known commercially as the GRAFTON® Putty and Flex, respectively.

The use of the very low molecular weight glycerol carrier also requires a very high concentration of glycerol to be used to achieve the bulk viscosity. Glycerol and other similar low molecular weight organic solvents are toxic and irritating to the surrounding tissues.

U.S. Pat. No. 5,356,629 discloses making a rigid gel in the nature of a bone cement to fill defects in bone by mixing biocompatible particles preferably polymethylmethacrylate coated with polyhydroxyethylmethacrylate in a matrix selected from a group which lists hyaluronic acid to obtain a molded semi-solid mass which can be suitably worked for implantation into bone. The hyaluronic acid can also be utilized in monomeric form or in polymeric form preferably having a molecular weight not greater than about one million Daltons. It is noted that the nonbioabsorbable material which can be used to form the biocompatible particles can be derived from xenograft bone, homologous bone, autogenous bone as well as other materials. The bioactive substance can also be an osteogenic agent such as demineralized bone powder, in addition to morselized cancellous bone, aspirated bone marrow and other autogenous bone sources. The average size of the particles employed is preferably about 0.1 to about 3.0 mm, more preferably about 0.2 to about 1.5 mm, and most preferably about 0.3 to about 1.0 mm. It is inferentially mentioned but not taught that particles having average sizes of about 7,000 to 8,000 microns, or even as small as about 100 to 700 microns can be used. However, the biocompatible particles used in this reference are used in a much greater weight ranging from 35% to 70% by weight then that taught by the present invention. This is simply a cement used for implantation of hip prosthesis and is not used to promote bone growth.

U.S. Pat. No. 5,830,493 is directed toward a composite porous body (hyaluronic acid listed in a group of compounds) comprising a porous frame and a surface layer comprising a bioabsorbable polymer material formed on the surface. A bone morphogenetic protein (BMP) is carried on the surface and inside of the composite porous body. There is no demineralization of bone and the reference appears only to be relevant to show the addition of BMP to a bone forming graft.

Another attempt to solve the bone composition problem is shown in U.S. Pat. No. 4,172,128 which discloses demineralized bone material mixed with a carrier to reconstruct tooth or bone material by adding a mucopolysaccharide to a mineralized bone colloidal material. The composition is formed from a demineralized coarsely ground bone material, which may be derived from human bones and teeth, dissolved in a solvent forming a colloidal solution to which is added a physiologically inert polyhydroxy compound such as mucopolysaccharide or polyuronic acid in an amount which causes orientation when hydrogen ions or polyvalent metal ions are added to form a gel. The gel will be flowable at elevated temperatures above 35 C and will solidify when brought down to body temperature. Example 25 of the patent notes that mucopolysaccharides produce pronounced ionotropic effects and that hyaluronic acid is particularly responsible for spatial cross-linking. Unfortunately this bone gel is difficult to manufacture and requires a premolded gel form.

U.S. Pat. No. 4,191,747 teaches a bone defect treatment with coarsely ground, denatured bone meal freed from fat and ground into powder. The bone meal is mixed with a polysaccharide in a solution of saline and applied to the bone defect site.

Another prior art product is the formulation of demineralized allograft bone particles in collagen. Both bovine and human collagen have been used for this application. Bovine collagen carries the risk of an immunogenic reaction by the recipient patient. Recently, it has been found that a disease of cattle, bovine spongioform encephalopathy (BSE) is transmitted from bovine tissue to humans. Thus, bovine tissue carries a risk of disease transmission and is not a desirable carrier for allograft tissue.

Human collagen is free of these animal based diseases. However, collagen absorbs slowly in the human body, particularly in a bony site with usually a low degree of vascularity. The slow absorption of collagen can delay the growth of new bone and result in the formation of scar tissue at the site. This could result in a non-bony healing and a result with much less tensile strength.

Accordingly, the prior art as embodied in the glycerol and other carrier based technology to deliver demineralized allograft bone to a surgical osseous site is replete with problems and only partially addresses the problems inherent in the correcting surgical defects.

SUMMARY OF THE INVENTION

The subject formulation is a complex mixture of demineralized bone matrix (DBM) and a viscous hydrogel based on a very high molecular weight material with a sodium based phosphate buffer acting as a carrier or delivery vehicle for the therapeutic agent, DBM. The viscous formulation is designed to present the DBM, and its bone morphogenic proteins (BMP), and the macrostructure of the highly porous DBM itself to serve both as an osteoconductive matrix and to signal the patient's tissue and cells to initiate the growth of new bone (osteoinduction). The formulation is used primarily in contact with bleeding bone. This condition is created either from trauma or a surgical procedure, that may involve drilling, sawing, grinding or scraping the bone to achieve a bleeding condition. In surgery, the bone is traumatized or surgically cut exposing blood capillaries, Haversian canals (micro-channels in the bone), periosteum (the protective tissue lining around bone), muscle and other structures in the surgical site. Bleeding at the site is considered a favorable condition to enhance healing of the wound site by bringing to the site the patient's own cytokines, i.e., proteins and other molecules which are the body's mechanism to carry out the healing process. Any interference with the blood cell mechanism would be considered non-biocompatible and an adverse outcome.

In order for the DBM to be osteoinductive, interference either from the traumatized cells or the formulation must be at a minimum, i.e., a biocompatible condition should be established and maintained. Several specific properties have been established in the formulation to create a functional and therapeutic material. These properties pertain to both physical characteristics and to the achieving of a biocompatible or physiologically friendly condition.

The selection of high molecular weight hydrogels allows the use of the preferred small particle size granules of demineralized allograft bone. These small particles pack better in the wound defect and absorb quickly thereby allowing the bone defect to be remodeled into the natural bone of the patient.

It is an object of the invention to utilize demineralized powdered bone in a particle size that is useful to achieve the malleability characteristics that maximizes the amount of bone in the formulation without creating a gritty, less malleable characteristic.

It is an additional object of the invention to use a non toxic aqueous solution carrier with a sodium phosphate buffer for the bone particles to present the composition in a state of physiological osmolality at the wound site.

It is also an object of the invention to create a bone defect material which can be easily handled by the physician and does not degenerate when contacting blood flow at the surgical site.

It is another object of the invention to create a bone defect material which does not interfere with healing at the wound site.

It is still another object of the invention to create a bone defect material which has a stable viscosity from 22° to 37° C.

It is an additional object of the invention to create a bone defect material with an isotonic pH.

It is yet another object of the invention to use a sodium salt with the demineralized bone composition to aid in healing at the bone defect site.

In other embodiments the invention provides a premixed bone putty/gel in a protected carrier to keep the putty/gel from drying out or being degraded.

DESCRIPTION OF THE INVENTION

The present invention is directed towards a demineralized bone powder composition to heal bone defects.

A bone putty and gel with a useful bulk viscosity has been achieved by using a very high molecular weight class of soluble biomaterial, hydrogel. The use of high molecular weight hydrogels preferably over 500,000 Daltons allows the achievement of a useable bone gel with a 0.50–1.5% concentration of the hydrogel in the carrier and a malleable bone putty with a 2.0–5.0% concentration of the hydrogel in the carrier. The balance of the carrier formulation is an aqueous solution and preferably includes the addition of a material component, namely, a sodium based phosphate buffer in a sterile saline or salt carrying water which avoids the toxic problems with the high concentrations of the low molecular weight organic solvents of the prior art.

The combination of the 250–710 micron particle size of demineralized, lyophilized, allograft bone when mixed with very low concentrations of very high molecular weight stable viscosity hydrogels in a suitable carrier produces a malleable putty with clinically useful bone inducing properties. The malleable property permits the surgeon to shape the quantity of bone putty or gel to exactly fit the surgical defect. Manipulation of the "lump" of bone putty may be done without it sticking to the gloves of the surgeon, behaving somewhat like a wet clay used in sculpting.

It is an important aspect of the present invention that the implant matrix must remain at the wound site and not be washed away by the flowing blood and other fluids brought to the site by the healing mechanism. This is achieved by both the viscous and hydrogel state of the carrier. While viscous, the aqueous carrier is a high molecular weight macromolecule held together with water linkages (hydrogen bonds) and is not readily dissolved and washed away by the blood and fluids at the wound site.

Thus, the therapeutic DBM will not be dissipated by being washed away and will be present to be osteoinductive.

The amount of DBM is maximized to achieve the optimum balance of osteoinductivity and physical handling properties. Too much matrix bone creates a gritty or sandy condition in which the DBM is not ideally enclosed by the surrounding viscous matrix and the DBM bone particles would be too easily washed away. Conversely, if the bone concentration is too low, the osteoinductivity would be less than optimum. Bone concentration in the composition is in the range of about 20% to about 50%.

These and other alternate embodiments of the invention overcome the two basic deficiencies of the glycerol carrier and bone particle flowable compositions used in the prior art: first, the low molecular weight of glycerol; and second, the use of large particles or lamellae to achieve the preferred bulk viscosity. The types of demineralized bone used in the invention are cortical and corticocancellous bone powder.

The primary role of the carrier is to serve as a delivery vehicle. The bulk viscosity of the carrier achieves the design goal of good handling properties by balancing the molecular weight and concentration of the hydrogel used in the formulation. For example, a very high molecular weight hydrogel would use a lower concentration compared to a formulation in which the hydrogel molecular weight was considerably lower with a higher concentration used to achieve the same bulk viscosity. The nominal formulation uses a 700,000 Dalton molecular weight hydrogel (sodium hyaluronate, or HA). This HA material is used at a 1–5% concentration in water or phosphate buffered saline to achieve the bulk viscosity required for the gel or putty formulation.

If the balance of molecular weight and concentration were not optimized, the results would be a runny, excessively fluid formulation that would not stay at the surgical site. While Hydrogel molecular weights as low as 150,000 Dalton with a concentration as high as about 10–15% would give a good bulk viscosity, concentrations with corresponding viscosity above this level cannot be filtered to achieve sterility required by a surgical implant. Guidelines for sterility require a statistical assurance of no more surviving microorganisms than one in one million. This cannot be achieved above a concentration of about 5–6% hydrogel of a molecular weight of 700,000 Dalton. Very much higher concentrations would result in a semi solid not having desirable handling properties as it would lose the desirable malleability required for a defect filling formulation.

Hydrogels of a higher molecular weight can also be effectively used at concentrations as low as 0.25 to 1.5% to achieve a successful bulk viscosity of 120,000 to 270,000 for putty and 2,000 to 15,000 for gel. At these concentrations, molecular weights of the hydrogel as high as 3–5 million Dalton can be used.

The ideal carriers for the malleable putty are preferably taken from high molecular weight hydrogels such as 1) Sodium Hyaluronate about $7.0 \times 10^5 - 3.0 \times 10^6$ Daltons.

The molecular weight of the hydrogels used in the carriers set forth in the Examples are: Sodium hyaluronate—($7.0 \times 10^5$ to $2.4 \times 10^6$ Daltons); N,O-carboxymethylchitosan glycosaminoglycan hydrogel derivative.—$2.0 \times 10^6 - 3.0 \times 10^6$ Daltons.

The natural condition for blood plasma as well as synovial fluid, cerebrospinal fluid, aqueous humor (fluid within the globe of the eye) is at a pH of 7.3–7.4 (reference, *Principles of Biochemistry*, Chapters 34 & 35; White, Handler and Smith, McGraw Hill, N.Y., 1964). At very slight changes in pH, blood cells will shift their equilibrium of hemoglobin. This hemoglobin concentration will change over the small pH range of 7.3 to 7.7 (White et al p. 664). In addition, at significantly lower pH values in the acidic range, protein molecules will denature, i.e., degrade. Thus, it is important to maintain any surgical implant which is intimate contact with blood at a biocompatible condition of about pH 7.2–7.4.

It is important to note that the body has many complex and redundant mechanisms to maintain its biochemical balance. The blood pH can be adjusted by several means to its normal, physiologic pH. Hence the presence of a non-physiologic material at the site of a bleeding bone wound will eventually be overcome and any non-biocompatible condition will return to normal pH. It is the teaching of this invention that the preferred formulation will start out and maintain physiologic pH without stressing the body's biochemical mechanisms when the bone composition material is applied at the wound site.

In achieving physiologic pH, the formulation uses a phosphate buffer based on an aqueous system of the two phosphate anions, $HPO_4^{-2}$ and $H_2PO_4^{-1}$. This buffer system is used both to neutralize the acid used to demineralize the bone and to buffer the sodium hyaluronate viscous hydrogel carrier. It is important to neutralize the acid (hydrochloric acid) used to demineralize the bone so as to assure that there is no residue of this very strong acid which could overwhelm the buffering capacity of the phosphate system used to buffer the sodium hyaluronate carrier.

The pH is adjusted to the physiologic 7.2–7.4 pH by using either or both of dibasic sodium phosphate or monobasic sodium phosphate and adjusting the solution with saline, i.e., a sodium chloride solution. The sodium chloride is chosen instead of only water so as to control the final osmolality of the formulation to preclude dehydration of the surrounding cells.

The present invention uses sodium salts of the phosphate buffer. This is to create an equilibrium system at the wound site which will draw in calcium ions necessary to grow new bone. The mechanism to achieve this is based on the LeChatelier corollary to the *Principle of Chemical Equilibrium*: When a factor (temperature, pressure, concentration, etc.) determining the equilibrium of a system is altered, the system tends to change in such a way as to oppose and partially annul the alteration in this factor. (reference, *General Chemistry*, McCutcheon, Seltz and Warner, Van Nostrand, N.Y., 1944; p. 248).

This principal manifests at the bone wound site as follows: The buffer introduced contains sodium and phosphate ions which will remain in solution due to the high solubility of sodium phosphate. Calcium ions in the extracellular fluid will react with the phosphate ions to result in the precipitation of insoluble calcium phosphate salt. More phosphate ions will ionize from the associated state of the phosphate buffer to introduce more phosphate ions that will, in turn react with more calcium and precipitate yet more insoluble calcium phosphate. The calcium phosphate will deposit at the wound site where the buffered formulation was placed by the surgeon. This results in an increase in the presence of calcium at the wound site. The bone regeneration mechanism will utilize calcium starting 7–10 days after the wound starts healing by the well-known osteochondral healing mechanism. Hence, the selection of the sodium phosphate buffer to achieve the physiologic pH provides a means to increase the calcium concentration in the precise location where calcium will be needed to grow new bone.

Thus, the invention induces the presence of soluble calcium at the bone defect site. This will encourage new bone growth through the normal biochemical mechanism. Soluble calcium can be attracted to the surgical site by using a sodium phosphate buffer of pH 6.8–7.2 in lieu of isotonic saline. The phosphate buffer attracts calcium cations to the site from the surrounding healthy bone and creates an equilibrium concentration of the calcium precisely at the site of healing where it is most desirable to grow new bone.

It is a well known principal of physiology that osmotic pressure must be maintained within a narrow range to assure healthy conditions for the many cell types present in normal or surgically wounded cells. The condition of normal osmotic pressure is referred to as an isotonic state and is quantified in humans by the value of about 300 mOsmol/Kg. The sodium hyaluronate (HA) formulation is buffered to isotonic conditions using sodium chloride as the ionic salt to supplement the sodium phosphate. Were the sodium hyaluronate formulation to be buffered without the supplemental saline, the final hydrogel would only reach an osmolality of less than 50 mOsmol/Kg.

At this low osmolality, the extra cellular environment at the wound site would be in a state of hypotonicity and result in the inflow of large quantities of water to the cells and blood cells at the wound site to normalize the osmotic pressure. This will result in a greater than optimum degree of hydration of the cells and inhibit wound healing in general and bone growth in particular. Hemolysis may occur due to excess fluid in the cells.

Other, commercial bone defect fillers are either non-isotonic or worse, are completely anhydrous. The anhydrous state will result in a massive hydration of the site. This will result in an edematous condition. This condition would result in both diluting the DBM (washes it away) and massive dilution of the extracellular fluids. On a macro level, edema is seen as swelling at the site and may be painful to the patient.

The subject formulation has been tested for resistance to hemolysis in a test based on direct blood contact; the results were negative, i.e., the formulation was found to be non-hemolytic. The commercial, anhydrous formulation based on anhydrous glycerol is hemolytic by the same test protocol. The observation of hemolytic behavior by the glycerol based commercial bone filler may be due to the acidic pH (about 4.5) alone, or to a combination of the acidic pH and the non-isotonic state of the material as it enters the wound site.

Sodium hyaluronate in the form of the sodium salt is generally described as an acid mucopolysaccharide. It is envisioned that suitable amounts of bone morphogenic proteins (BMP) can be added to either the gel or putty at any stage in the mixing process to induce accelerated healing at the bone site. BMP directs the differentiation of pluripotential mesenchymal cells into osteoprogenitor cells which form osteoblasts. The ability of freeze dried demineralized cortical bone to transfer this bone induction principle using BMP present in the bone is well known in the art. However, the amount of BMP varies in the bone depending on the age of the bone donor and the bone processing. Sterilization is an additional problem in processing human bone for medical use as boiling, autoclaving and irradiation over 2.0 mrads is sufficient to destroy or alter the BMP present in the bone matrix.

In conducting experiments, it was found that a gel product with optimal formability and handling properties could have a sodium hyaluronate molecular weight ranging from 690,0000 to 1,200,000 Daltons with a sodium hyaluronate concentration ranging from 0.75–2.0% with a bone concentration ranging from 25–27% with a particle size of 100–820 microns. This resulted in HA solution viscosities ranging from about 1,800 cps to about 13,000 cps. It was also found that a putty product with optimal formability and handling properties would have a molecular weight ranging from 690,000 to 1,200,000 Daltons with a sodium hyaluronate concentration ranging from 2.0–4.5% with a bone concentration ranging from 30–33% with a particle size of 100–820 microns. This resulted in HA solution viscosities ranging from about 6,000 cps to about 275,000 cps.

Any number of medically useful substances can be used in the invention by adding the substances to the composition at any steps in the mixing process or directly to the final composition. Such substances include collagen and insoluble collagen derivatives, hydroxy apatite and soluble solids and/or liquids dissolved therein. Also included are antiviricides such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin and gentamycin. It is also envisioned that amino acids, peptides, vitamins, co-factors for protein synthesis; hormones; endocrine tissue or tissue fragments; synthesizers; enzymes such as collagenase, peptidases, oxidases; polymer cell scaffolds with parenchymal cells; angiogenic drugs and polymeric carriers containing such drugs; collagen lattices; biocompatible surface active agents, antigenic agents; cytoskeletal agents; cartilage fragments, living cells such as chondrocytes, bone marrow cells, mesenchymal stem cells, natural extracts, tissue transplants, bioadhesives, transforming growth factor (TGF-beta), insulin-like growth factor (IGF-1); growth hormones such as somatotropin; bone digestors; antitumor agents; fibronectin; cellular attractants and attachment agents; immuno-suppressants; permeation enhancers, e.g. fatty acid esters such as laureate, myristate and stearate monoesters of polyethylene glycol, enamine derivatives, alpha-keto aldehydes can be added to the composition.

The invention can be further understood by the following examples with the percentages being determined by weight. In some samples as shown by Tables 1–4, a penetration test was used to measure the bulk consistency of the formulation. In principle, the test measures the depth of penetration of a metal cone of a known mass inserted into a sample of the formulation for a fixed time. The heavier a formulation the less penetration occurs. This test is adopted from ASTM Method D 1403-96: Standard Test Method for Cone preparation Lubricating Grease Using One Quarter and One-Half Scale Cone Equipment. It was found that as the viscosity increases, penetration decreases and when the viscosity is the same, the increase in percentage of bone particle weight results in a decrease of penetration. All examples could also be done in an aseptic environment to maintain a sterile final product.

SUMMARY OF PENETRATION RESULTS

Tables 1 and 2 show the penetration data of samples prepared with HA with a molecular weight of 690,000 Daltons. The sample numbers are not in numeric order because they are placed in the order from the lowest HA viscosity to the highest viscosity. When viscosity is the same for two samples, the samples are arranged from the lower % FDDB concentration to the higher % FDDB concentration. The additional weight column shows how much (if any) additional weight was added to the plunger before the testing interval. Additional weight can be placed on top of the plunger for deeper penetration and more accurate readings when testing hard materials.

TABLE 1

Penetration Data of Gel Samples Prepared With HA (Molecular Weight 690,00 Daltons)

| Sample Number | Composition | Viscosity of HA (cps) | additional weight | Penetration Averages (0.1 mm) | Standard Deviation |
|---|---|---|---|---|---|
| 6-72-13 | 25% FDDB in 1.2% HA | 2,070 | 0 g | 83 | 1 |
| 6-73-19 | 27% FDDB in 1.2% HA | 2,070 | 0 g | 65 | 1 |
| 6-72-14 | 25% FDDB in 1.3% HA | 3,210 | 0 g | 80.3 | 0.58 |
| 6-73-20 | 27% FDDB in 1.3% HA | 3,210 | 0 g | 62.3 | 0.58 |
| 6-91-A | 25% FDDB in 1.5% HA | 4,900 | 0 g | 75 | 1 |
| 6-91-B | 27% FDDB in 1.5% HA | 4,900 | 0 g | 60.3 | 0.58 |
| 6-72-15 | 25% FDDB in 1.7% HA | 7,730 | 0 g | 72.3 | 0.58 |
| 6-73-21 | 27% FDDB in 1.7% HA | 7,730 | 0 g | 56.7 | 0.58 |
| 6-72-16 | 25% FDDB in 1.8% HA | 10,400 | 0 g | 65 | 1 |

TABLE 1-continued

Penetration Data of Gel Samples Prepared With HA
(Molecular Weight 690,00 Daltons)

| Sample Number | Composition | Viscosity of HA (cps) | additional weight | Penetration Averages (0.1 mm) | | Standard Deviation |
|---|---|---|---|---|---|---|
| 6-73-22 | 27% FDDB in 1.8% HA | 10,400 | 0 g | | 54.7 | 1.15 |
| 6-66-3 | 25% FDDB in 2.0% HA | 14,900 | 0 g | 60.7 | | 0.58 |
| 6-66-4 | 27% FDDB in 2.0% HA | 14,900 | 0 g | | 54.3 | 1.15 |

TABLE 2

Penetration Data of Putty Sample Prepared With HA
(Molecular Weight: 690,000 Daltons)

| Sample Number | Composition | Viscosity of HA (cps) | additional weight | Penetration Averages (0.1 mm) | | Standard Deviation |
|---|---|---|---|---|---|---|
| 6-66-5 | 30% FDDB in 3.5% HA | 118,000 | 50 g | 63.7 | | 1.15 |
| 6-66-6 | 33% FDDB in 3.5% HA | 118,000 | 50 g | | 60 | 1.73 |
| 6-72-17 | 30% FDDB in 3.75% HA | 146,000 | 50 g | 62 | | 1 |
| 6-73-23 | 33% FDDB in 3.75% HA | 146,000 | 50 g | | 58.3 | 1.15 |
| 6-66-11 | 30% FDDB in 4.0% HA | 185,000 | 50 g | 59.3 | | 0.58 |
| 6-66-12 | 33% FDDB in 4.0% HA | 185,000 | 50 g | | 55 | 1 |
| 6-72-18 | 30% FDDB in 4.25% HA | 222,800 | 50 g | 57.7 | | 1.53 |
| 6-73-24 | 33% FDDB in 4.25% HA | 222,800 | 50 g | | 53.7 | 0.58 |
| 6-66-7 | 30% FDDB in 4.5% HA | 260,600 | 50 g | 55 | | 1 |
| 6-66-8 | 33% FDDB in 4.5% HA | 260,600 | 50 g | | 51.3 | 0.58 |

These tables show that as the viscosity increases, penetration decreases. They also show that when the viscosity is the same for two samples, the increase in % FDDB results in a decrease of penetration.

Tables 3 and 4 show the penetration data of samples prepared with HA with a Molecular Weight of $1.2 \times 10^6$ Daltons. The samples are placed in the order from the lowest HA viscosity to the highest viscosity. When the viscosity is the same for two samples, the samples are arranged from the lower % FDDB concentration to the higher % FDDB concentration. The additional weight column shows how much (if any) additional weight was added to the plunger before the testing interval. Additional weight can be placed on top of the plunger for deeper penetration and more accurate readings when testing hard materials.

TABLE 3

Penetration Data of Gel Samples Prepared with HA
(Molecular Weight: $1.2 \times 10^6$ Daltons)

| Sample Number | Composition | Viscosity of HA (cps) | additional weight | Penetration Averages (0.1 mm) | | Standard Deviation |
|---|---|---|---|---|---|---|
| 6-79-1 | 25% FDDB in 0.75% HA | 1,840 | 0 g | 72 | | 1.73 |
| 6-79-2 | 27% FDDB in 0.75% HA | 1,840 | 0 g | | 65.7 | 0.58 |
| 6-79-3 | 25% FDDB in 0.85% HA | 3,150 | 0 g | 69 | | 1 |
| 6-79-4 | 27% FDDB in 0.85% HA | 3,150 | 0 g | | 55.7 | 1.15 |
| 6-79-5 | 25% FDDB in 1.0% HA | 6,000 | 0 g | 65 | | 1 |
| 6-79-6 | 27% FDDB in 1.0% HA | 6,000 | 0 g | | 52.3 | 1.53 |
| 6-79-7 | 25% FDDB in 1.15% HA | 9,950 | 0 g | 58 | | 1.73 |
| 6-79-8 | 27% FDDB in 1.15% HA | 9,950 | 0 g | | 51.3 | 0.58 |
| 6-79-9 | 25% FDDB in 1.25% HA | 13,100 | 0 g | 57.3 | | 0.58 |
| 6-79-10 | 27% FDDB in 1.25% HA | 13,100 | 0 g | | 48.3 | 1.53 |

TABLE 4

Penetration Data of Putty Samples Prepared With HA
(Molecular Weight: $1.2 \times 10^6$ Daltons)

| Sample Number | Composition | Viscosity of HA (cps) | additional weight | Penetration Averages (0.1 mm) | | Standard Deviation |
|---|---|---|---|---|---|---|
| 6-80-11 | 30% FDDB in 2.4% HA | 124,000 | 50 g | 61.7 | | 1.15 |
| 6-80-12 | 33% FDDB in 2.4% HA | 124,000 | 50 g | | 56.7 | 0.58 |
| 6-80-13 | 30% FDDB in 2.5% HA | 142,000 | 50 g | 59.3 | | 1.53 |
| 6-80-14 | 33% FDDB in 2.5% HA | 142,000 | 50 g | | 54.7 | 0.58 |

TABLE 4-continued

Penetration Data of Putty Samples Prepared With HA
(Molecular Weight: 1.2 × 10⁶ Daltons)

| Sample Number | Composition | Viscosity of HA (cps) | additional weight | Penetration Averages (0.1 mm) | | Standard Deviation |
|---|---|---|---|---|---|---|
| 6-80-15 | 30% FDDB in 2.65% HA | 169,000 | 50 g | 58.3 | | 1.53 |
| 6-80-16 | 33% FDDB in 2.65% HA | 169,000 | 50 g | | 53.3 | 0.58 |
| 6-80-17 | 30% FDDB in 2.8% HA | 228,400 | 50 g | 57 | | 1 |
| 6-80-18 | 33% FDDB in 2.8% HA | 228,400 | 50 g | | 52 | 1 |
| 6-80-19 | 30% FDDB in 3.1% HA | 273,000 | 50 g | 56.7 | | 1.15 |
| 6-80-20 | 33% FDDB in 3.1% HA | 273,000 | 50 g | | 49 | 1 |

These tables show that as the viscosity increases, penetration decreases. It also shows that when the viscosity is the same for two samples, the increase in % FDDB results in a decrease of penetration.

ADDITIONAL EXAMPLES OF THE INVENTION

In the following examples the molecular weight of the various carrier components used is as follows:

| 1) Sodium Hyaluronate | $7.0 \times 10^5 - 2.6 \times 10^6$ Daltons |
|---|---|

Example I

A malleable putty of 2% solution sodium hyaluronate in isotonic saline with 250–420 micron cortical allograft bone demineralized powder @30%.

502 milligrams of freeze dried demineralized cortical allograft bone of particle size ranging from 250–420 microns was mixed into 1,170 milligrams of a 2% solution of sodium hyaluronate in isotonic saline with a phosphate buffer. The bone component is added to achieve a bone concentration of 30% (w/w). The mixture was well stirred and allowed to stand for 2–3 hours at room temperature to provide a malleable putty with excellent formability properties.

Example II

A malleable putty of 3% solution sodium hyaluronate with 100–300 micron demineralized cortical allograft bone powder @33%.

720 milligrams of freeze dried demineralized cortical allograft bone of particle size of 100–300 microns was mixed into 1,402 milligrams of a 3% solution of sodium hyaluronate in an aqueous solution of a sodium chloride based phosphate buffer having a viscosity ranging from about 230,000 to about 275,000. The bone component is added to achieve a bone concentration of 33%(w/w). The mixture was well stirred and allowed to stand for 2–3 hours at room temperature. This provided a malleable putty with excellent formability properties.

Example III

A malleable putty of 1% solution sodium hyaluronate with 250–420 micron demineralized cortical allograft bone powder @40%.

605 milligrams of freeze dried demineralized cortical allograft bone of particle size of 250–420 microns was mixed into 906 milligrams of a 1% solution of sodium hyaluronate in isotonic saline with a phosphate buffer. The bone component was added to achieve a bone concentration of 40%(w/w). The mixture was well stirred and allowed to stand for 2–3 hours at room temperature. This provided a malleable putty with poor formability properties.

Example IV

A flowable gel of 250–420 micron particle size demineralized cortical allograft bone granules in a 1% solution of sodium hyaluronate at a 25%(w/w) of bone content.

503 milligrams of allograft freeze dried demineralized cortical bone was mixed into 1,502 milligrams of a 1% solution of sodium hyaluronate having a viscosity ranging from 2,000 cps to 6,000 cps in an aqueous solution of a sodium chloride based phosphate buffer. The mixture was well stirred and allowed to stand at room temperature to provide a flowable gel.

Example V

A flowable gel of 250–420 micron particle size demineralized cortical allograft granules in a 1% solution of sodium hyaluronate at a 30%(w/w) of bone content.

501 milligrams of allograft freeze dried demineralized cortical bone was mixed into 1,167 milligrams of a 1% solution of sodium hyaluronate in isotonic saline phosphate buffer. The bone component is added to achieve a bone concentration of 30%(w/w). The mixture was well stirred and allowed to stand for 2–3 hours at room temperature. This provided a flowable gel.

Example VI

A flowable gel of 420–850 micron particle size demineralized cortical allograft granules in a 1% solution of sodium hyaluronate at a 25%(w/w) of bone content.

501 milligrams of allograft freeze dried demineralized cortical bone was mixed into 1,501 milligrams of a 1% solution of sodium hyaluronate in isotonic saline phosphate buffer. The bone component is added to achieve a bone concentration of 25%(w/w). The mixture was well stirred and allowed to stand for 2–3 hours at room temperature. This provided a flowable gel.

Example VII

A flowable gel of 420–850 micron particle size demineralized cortical allograft granules in a 1% solution of sodium hyaluronate at a 30%(w/w) of bone content.

500 milligrams of allograft freeze dried demineralized cortical bone was mixed into 1,166 milligrams of a 1% solution of sodium hyaluronate in isotonic saline phosphate buffer. The bone component is added to achieve a bone concentration of 30%(w/w). The mixture was well stirred and allowed to stand for 2–3 hours at room temperature. This provided a flowable gel.

Example VIII

A malleable putty of 250–710 micron particle size demineralized cortical allograft granules in a 4.4% solution of sodium hyaluronate at a 30% (w/w) of bone content. 90 grams of freeze-dried demineralized cortical allograft bone were mixed into 210 grams of a 4.4% solution of sodium hyaluronate (660,000 Daltons) in phosphate buffered saline with pH 7.3, viscosity of 207,000 cps and osmolality of 337 mOsmol/Kg. The bone component was added to achieve a bone concentration of 30% (w/w). The mixture was well mixed and allowed to stand for 2–3 hours at room temperature. This provided a malleable putty.

Example IX

A flowable gel of 250–710 micron particles of demineralized cortical allograft granules in a 1.9% solution of sodium hyaluronate at 25% (w/w) of bone content. 75 g of freeze-dried demineralized cortical allograft bone was mixed into 225 g of 1.9% solution of sodium hyaluronate (660,000 Daltons) in phosphate buffered saline with pH 7.3, viscosity of 8,700 cps and osmolality of 314 mOsmol/Kg. The bone component was added to achieve a bone concentration of 25% (w/w). The mixture was well mixed and allowed to stand for 2–3 hours at room.

A flowable gel can be made up of about 25–30% demineralized bone powder (particle size in a range of 250–850 microns) mixed into a high molecular weight hydrogel carrier in solution, such as 2% sodium hyaluronate.

A putty can be made up of about 30–35% demineralized bone powder (particle size in a range of 250–850 microns) mixed into a high molecular weight hydrogel carrier in solution, such as 5% sodium hyaluronate.

One process commonly used to achieve sterility is sterile filtration of the sodium hyaluronate (HA) followed by aseptic mixing of the bone and HA. Another method is to irradiate the HA material first and then continue with aseptic mixing of the bone. Irradiation sources of either electron beam or gamma (Cobalt 60 isotope) are commercially available.

The use of radiation will reduce the molecular weight of the HA. An HA with much higher molecular weight up to 6,000,000 Daltons would be selected and the irradiation controlled to reduce the molecular weight to a level sufficient to achieve the desired final viscosity. This approach expands the available range of HA molecular weight and concentration useful for the invention.

The mixing of the demineralized bone powder into hydrogel solution is undertaken in a sterile chamber. The mixed malleable bone composition is then placed in a sterile container such as an impervious syringe barrel or vial, sealed and placed in a sterile sealed package.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What we claim is:

1. A sterile formable bone composition for application to a bone defect site to promote new bone growth at the site comprising a mixture of demineralized osteoinductive and osteoconductive bone powder with a particle size ranging from about 100 to about 850 microns in an aqueous carrier solution, the bone powder ranging from about 25 to about 35% of the weight of the composition, the carrier comprising a hydrogel component of sodium hyaluronate in a phosphate buffered aqueous solution, said hydrogel component having a high molecular weight ranging from over six hundred thousand to three million Daltons with a stable viscosity at a temperature range from about 22° to about 37° C. and ranging from about 0.75% to about 5.0% by weight of the aqueous carrier solution, said composition having a pH ranging from about 6.8 to about 7.4.

2. A sterile formable bone composition as claimed in claim 1 wherein said mixture includes bone morphogenic protein in excess of the amount naturally occurring in allogeneic bone.

3. A sterile formable bone composition as claimed in claim 1 wherein said phosphate includes two phosphate ions $HPO_4^{-2}$ and $H_2PO_4^{-1}$.

4. A sterile formable bone composition as claimed in claim 1 wherein said composition has an isotonic state of about 300 mOsmol/Kg.

5. A sterile formable bone composition as claimed in claim 1 wherein said bone powder contains cortical allograft bone powder.

6. A sterile formable bone composition as claimed in claim 1 wherein said bone powder contains corticalcancellous bone powder.

7. A sterile formable bone composition as claimed in claim 1 wherein the aqueous carrier solution includes an ionic salt based phosphate buffer.

8. A sterile formable bone putty composition for application to a bone defect site to promote new bone growth at the site which comprises a new bone growth inducing mixture of demineralized lyophilized allograft bone powder with a particle size ranging from about 250 to about 710 microns in sodium hyaluronate with an ionic salt based phosphate buffer carrier causing the composition to have a pH ranging between about 6.8 and about 7.4, the sodium hyaluronate component having a molecular weight of at least six hundred and sixty thousand Daltons and a stable viscosity ranging from 6,000 to about 275,000 cps at a temperature range of 22° to 37° C., the bone content of the carrier ranging in weight from about 20% to less than 50% total weight of the composition.

9. A sterile formable bone putty composition as claimed in claim 8 wherein said saline phosphate buffer carrier includes a sodium based phosphate compound.

10. A sterile formable bone putty composition as claimed in claim 8 wherein said phosphate includes two phosphate ions $HPO_4^{-2}$ and $H_2PO_4^{-1}$.

11. A sterile formable bone putty composition as claimed in claim 8 wherein said composition has an isotonic state of about 300 mOsmol/Kg.

12. A sterile formable bone putty composition as claimed in claim 8 wherein said sodium hyaluronate has been irradiated.

13. A sterile formable bone putty composition as claimed in claim 8 including antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin, gentamycin and vitamins.

14. A sterile formable bone putty composition as claimed in claim 8 wherein said mixture includes bone morphogenic proteins in excess of the amount naturally occurring in allogeneic bone.

15. A formable bone putty composition for application to a bone defect site to promote new bone growth at the site comprising a new bone growth inducing demineralized lyophilized allograft bone powder with a particle size ranging from about 250 to about 710 microns in a high molecular weight sodium hyaluronate and saline phosphate buffer carrier, the bone demineralized content of the composition ranging from about 30% to about 35% by weight and the high molecular weight sodium hyaluronate component being sterile and constituting a percentage of the carrier not in excess of 5% of the weight of the carrier and has a molecular weight greater than 600,000 Daltons.

16. A sterile formable bone gel composition for application to a bone defect site to promote new bone growth at the site which comprises a new bone growth inducing amount of demineralized lyophilized allograft bone powder with a particle size ranging from about 250 to about 800 microns in a high molecular weight sodium hyaluronate having a molecular weight of at least about six hundred and sixty thousand Daltons in saline phosphate buffer carrier with the sodium hyaluronate component comprising about 75% to about 2.5% of the carrier weight and having a viscosity of about 1,800 to 13,000 cps, the bone powder content of the composition ranging from about 25% to about 30% with said composition having an osmolality ranging from about 280 to about 340 mOsmol/Kg.

17. A sterile formable bone gel composition as claimed in claim 16 wherein said composition includes bone morphogenic proteins in excess of the amount naturally occurring in allogeneic bone.

18. A sterile formable bone gel composition as claimed in claim 16 wherein said phosphate includes two phosphate ions $HPO_4^{-2}$ and $H_2PO_4^{-1}$.

19. A sterile formable bone gel composition as claimed in claim 16 wherein said bone powder contains cortical allograft bone powder.

20. A sterile formable bone gel composition as claimed in claim 16 wherein said bone powder contains corticalcancellous allograft bone powder.

21. A sterile formable bone putty composition for application to a bone defect site to promote new bone growth at the site which comprises a new bone growth inducing compound of demineralized lyophilized allograft bone powder with a particle size ranging from about 250 to about 710 microns in a hydrogel ionic salt based phosphate buffer carrier, the hydrogel component comprising sodium hyaluronate and its derivatives and ranging from about 2.0% to about 5.0% by weight of the carrier and having a molecular weight of at least 600,000 Daltons, said composition having a pH ranging from 6.8 to 7.4.

22. A sterile formable bone putty composition for application to a bone defect site to promote new bone growth at the site which comprises a new bone growth inducing amount of demineralized lyophilized allograft bone powder in a high molecular weight hydrogel in saline phosphate buffer solution carrier, said hydrogel comprising an acid mucopolysaccharide having a molecular weight of at least 700,000 Daltons, the bone amount content of the composition ranging from about 30% to about 38% by weight and the high molecular weight hydrogel ranging from about 2.0% to about 5.0% by weight of the carrier, said composition having an osmolality ranging from 280–340 mOsmol/Kg.

23. A sterile formable bone putty composition for application to a bone defect site to promote new bone growth at the site which comprises a new bone growth inducing amount of demineralized lyophilized allograft bone powder in a high molecular weight hydrogel and saline phosphate buffer solution carrier, said hydrogel comprising an acid mucopolysaccharide having a molecular weight of at least 600,000 Daltons, the bone amount content of the composition ranging from about 30% to about 35% by weight and the high molecular weight hydrogel ranging from about 2.0% to about 4.0% by weight of the carrier, said composition having a pH ranging from about 7.2 to about 7.4.

24. A sterile formable bone putty composition for application to a bone defect site to promote new bone growth at the site which comprises a new bone growth inducing amount of demineralized lyophilized human allograft bone powder carrier in a high molecular weight hydrogel and saline phosphate buffer solution carrier, said hydrogel comprising an sodium hyaluronate having a molecular weight of at least 3,000,000 Daltons, the bone amount content of the composition ranging from about 30% to about 38% by weight and the high molecular weight hydrogel ranging from about 0.25% to about 1.5% by weight of the carrier, said composition having a pH ranging from about 6.8 to about 7.4.

25. A sterile formable bone putty composition as claimed in claim 24 wherein said carrier has a stable viscosity ranging from 120,000 to 275,000 cps at a temperature range from about 22° to about 37° C.

26. A sterile formable bone composition as claimed in claim 1 including an additive of living cells such as chondrocytes, bone marrow cells and mesenchymal stem cells.

27. A sterile formable bone composition as claimed in claim 1 including an additive of at least one growth factor.

28. A sterile formable bone composition as claimed in claim 1 wherein said bone powder contains cancerous bone powder.

29. A sterile formable bone putty composition as claimed in claim 23 including an additive of living cells such as chondrocytes, bone marrow cells and mesenchymal stem cells.

30. A sterile formable bone putty composition as claimed in claim 23 including an additive of at least one growth factor.

31. A sterile formable bone composition as claimed in claim 23 wherein said bone powder contains cancellous bone powder.

* * * * *